US010018534B2

(12) United States Patent
Zook et al.

(10) Patent No.: US 10,018,534 B2
(45) Date of Patent: Jul. 10, 2018

(54) ENVIRONMENTAL SAMPLING ARTICLES AND METHODS

(71) Applicant: 3M INNOVATIVE PROPERTIES COMPANY, St. Paul, MN (US)

(72) Inventors: Cynthia D. Zook, Hudson, WI (US); Robert H. Silbernagel, Easton, PA (US); Barbara L. Horter, Rochester, MN (US); Henry J. Lubrant, White Bear Lake, MN (US); Robert E. Koeritzer, Sun Prairie, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 560 days.

(21) Appl. No.: 14/476,158

(22) Filed: Sep. 3, 2014

(65) Prior Publication Data

US 2014/0370585 A1 Dec. 18, 2014

Related U.S. Application Data

(62) Division of application No. 12/743,528, filed as application No. PCT/US2008/084109 on Nov. 20, 2008, now Pat. No. 8,828,653.

(60) Provisional application No. 60/989,356, filed on Nov. 20, 2007.

(51) Int. Cl.
| | |
|---|---|
| *C12Q 1/04* | (2006.01) |
| *C12Q 1/00* | (2006.01) |
| *C12Q 1/06* | (2006.01) |
| *C12Q 1/24* | (2006.01) |
| *C12M 1/26* | (2006.01) |
| *C12M 1/16* | (2006.01) |
| *C12N 1/00* | (2006.01) |
| *C12N 1/18* | (2006.01) |
| *C12N 1/20* | (2006.01) |
| *G01N 1/02* | (2006.01) |
| *C12M 1/12* | (2006.01) |
| *C12M 1/34* | (2006.01) |

(52) U.S. Cl.
CPC ............. *G01N 1/02* (2013.01); *C12M 25/06* (2013.01); *C12M 41/36* (2013.01); *C12Q 1/04* (2013.01); *C12Q 1/24* (2013.01); *G01N 2001/028* (2013.01)

(58) Field of Classification Search
CPC ........................... G01N 1/02; G01N 2001/028
USPC ........ 435/34, 30, 243, 253.6, 255.21, 255.7, 435/256.8, 287.7, 287.9, 305.1, 39, 4
IPC ......... C12Q 1/04,1/00, 1/06, 1/24; C12M 1/26, 1/34, 1/16; B65D 85/00; C12N 1/00 , 1/18, 1/20, 1/24; G01N 1/02
See application file for complete search history.

(56) References Cited

U.S. PATENT DOCUMENTS

| | | | |
|---|---|---|---|
| 4,279,995 A | 7/1981 | Woods et al. | |
| 4,575,783 A | 3/1986 | Hammond | |
| 4,868,110 A | 9/1989 | DesRosier et al. | |
| 5,089,413 A | 2/1992 | Nelson et al. | |
| 5,118,750 A | 8/1992 | Silver | |
| 5,194,374 A | 3/1993 | Rambach | |
| 5,232,838 A | 8/1993 | Nelson et al. | |
| 5,348,884 A | 9/1994 | Kulla | |
| 5,364,766 A | 11/1994 | Mach et al. | |
| 5,385,826 A | 1/1995 | Schell et al. | |
| 5,403,722 A | 4/1995 | Floeder et al. | |
| 5,434,056 A | 7/1995 | Monget et al. | |
| 5,443,963 A | 8/1995 | Lund | |
| 5,462,860 A | 10/1995 | Mach | |
| RE35,286 E | 6/1996 | Nelson et al. | |
| 5,565,783 A * | 10/1996 | Lau ..................... | G01R 15/142 324/127 |
| 5,601,998 A | 2/1997 | Mach et al. | |
| 5,629,170 A | 5/1997 | Mondello | |
| 5,635,367 A | 6/1997 | Lund | |
| 5,681,712 A | 10/1997 | Nelson | |
| 5,730,167 A | 7/1998 | Tuompo et al. | |
| 6,002,789 A | 12/1999 | Olsztyn et al. | |
| 6,022,682 A | 2/2000 | Mach et al. | |
| 6,251,624 B1 | 6/2001 | Matsumura et al. | |
| 6,331,429 B1 | 12/2001 | Ushiyama | |
| 6,368,817 B1 | 4/2002 | Perry et al. | |
| 6,565,749 B1 | 5/2003 | Hou et al. | |
| 6,596,532 B1 | 7/2003 | Hyman et al. | |
| 6,617,149 B2 | 9/2003 | Restaino | |
| 6,638,755 B1 | 10/2003 | Mizuochi et al. | |
| 7,150,977 B2 | 12/2006 | Restaino | |
| 7,298,885 B2 | 11/2007 | Green et al. | |
| 7,298,886 B2 | 11/2007 | Plumb et al. | |
| 7,351,548 B2 | 4/2008 | Rambach | |

(Continued)

FOREIGN PATENT DOCUMENTS

| | | |
|---|---|---|
| EP | 0 398 703 | 11/1990 |
| EP | 0 454 046 | 10/1991 |

(Continued)

OTHER PUBLICATIONS

US 4,476,226, 10/1984, Hansen et al. (withdrawn)
3MPetrifilm ACP, 2006. Interpretation Guide. Use for Growing Lactic Acid Bacteria. © 3M 2006 70/2008-6506-4 (46.2 ii), 6 Pages.*
Blackburn et al. 1996. Evaluation of Petrifilm™ methods for enumeration of aerobic flora and coliforms in a wide range of foods. Letters in Applied Microbiology, vol. 22, pp. 137-140.*
Zimbro et al (Eds., 2009. Difco™ & BBL™ Manual, Manual of Microbiological Culture Media. 2nd Edition, BD Diagnostics, Diagnostic Systems, Sparks, MD 21152, p. 175, col. 2, Lines 32-48.*
Petrifilm™ Staph Express Count System Interpretation Guide, Published May 2002, 4 Pages.*

(Continued)

*Primary Examiner* — Louise Humphrey
*Assistant Examiner* — Kailash C Srivastava

(57) ABSTRACT

The present invention refers to articles for collecting samples from a surface, articles for microbiological analyses of said samples, and methods of use of said articles. The articles include sample collectors, sample housings with optional barrier layers, and sample-ready reagent strips comprising hydrophilic agents to grow and detect microorganisms. The disclosure includes methods to collect, detect, and quantify microorganisms in a surface sample.

8 Claims, 4 Drawing Sheets

(56) References Cited

U.S. PATENT DOCUMENTS

| | | | |
|---|---|---|---|
| 8,889,351 B2 * | 11/2014 | Mach | C12Q 1/04 435/34 |
| 2001/0041352 A1 | 11/2001 | Reilly et al. | |
| 2003/0088946 A1 | 5/2003 | Ferguson et al. | |
| 2003/0100104 A1 | 5/2003 | Jeffrey et al. | |
| 2004/0101954 A1 | 5/2004 | Graessle et al. | |
| 2004/0102903 A1 | 5/2004 | Graessle et al. | |
| 2005/0053266 A1 | 3/2005 | Plumb et al. | |
| 2006/0257967 A1 | 11/2006 | Restaino | |
| 2007/0259393 A1 | 11/2007 | Restaino | |
| 2008/0096195 A1 | 4/2008 | Rambach | |

FOREIGN PATENT DOCUMENTS

| | | | |
|---|---|---|---|
| GB | 1 494 358 | | 12/1977 |
| GB | 2 185039 A * | | 7/1987 |
| GB | 2185039 A * | 7/1987 | C12Q 1/04 |
| JP | H03-015379 | | 1/1991 |
| JP | 08-336381 | | 12/1996 |
| JP | 2001-321196 | | 11/2001 |
| JP | 2004-57054 | | 2/2004 |
| JP | 2006-230219 | | 9/2006 |
| WO | WO 1982-002563 | | 8/1982 |
| WO | WO 1992-007899 | | 5/1992 |
| WO | WO 1996-006183 | | 2/1996 |
| WO | WO 1996-038533 | | 12/1996 |
| WO | WO 1998-006870 | | 2/1998 |
| WO | WO 1998-033069 | | 7/1998 |
| WO | WO 1999-18232 | | 4/1999 |
| WO | WO 2000-053721 | | 9/2000 |
| WO | WO 2001-014583 | | 3/2001 |
| WO | WO 2002-046354 | | 6/2002 |
| WO | WO 2005-024047 | | 3/2005 |
| WO | WO 2005-062744 | | 7/2005 |
| WO | WO 2006-112709 | | 10/2006 |
| WO | WO 2007-023186 | | 3/2007 |
| WO | WO 2008-118400 | | 10/2008 |
| WO | WO 2008-150779 | | 12/2008 |
| WO | WO 2009-067498 | | 5/2009 |
| WO | WO 2009-067503 | | 5/2009 |
| WO | WO 2009-067513 | | 5/2009 |
| WO | WO 2009-067518 | | 5/2009 |
| WO | WO 2009-082667 | | 7/2009 |
| WO | WO 2010-147918 | | 12/2010 |
| WO | WO 2011-082305 | | 7/2011 |
| WO | WO 2012-092181 | | 7/2012 |

OTHER PUBLICATIONS

Baumgartner, A. et al."Quantitative Analysis of *E. coli* in Water Comparison of ECD Agar and Petrifilm™", Mitt. Gebiete Lebensm. Hyg.; vol. 84 1993, pp. 382-387.

Buhler, H.P. et al.; "Microbiological Evaluation of Drinking water: Modified Application of the 3M Petrifilm-Systems under Field Conditions", Schweiz Z. Milit. Med., vol. 70, No. 1, 1993; pp. 9-12.

Donofrio et al, "Evaluation of Four Membrane Filter Materials for Use with 3M™ Petrifilm™ *E. coli* Coliform Count Plates to Enumerate *Escherichia coli* in Water Samples"; (publication date unknown but believed to be prior to the date of the filing of the present application).

Ingham, C.J. et al. "Growth and Multiplexed Analysis of Microorganisms on a Subdivided, Highly Porous, Inorganic Chip Manufactured from Anapore", Applied and Environmental Microbiology, vol. 71, No. 12, 2005; pp. 8978-8981.

Nyachuba, D.G. et al.; "Comparison of 3M™ Petrifilm™ Environmental *Listeria* Plates against Standard Enrichment Methods for the Detection of *Listeria monocytogenes* of Epidemiological Significance from Environmental Surfaces"; Journal of Food Science, vol. 72, No. 9: 2007: pp. M346-M354.

Sadler, P.W. et al.; "Synthesis and Absorption Spectra of Symmetrical Chloroindigos", J. Am. Chem. Soc., vol. 78, 1956; pp. 1251-1255.

Sambrook, J. et al.; Molecular Cloning—A Laboratory Manual, Third Edition, vol. 2, Cold Spring Harbor Laboratory Press, Cold Spring Harbor, NY, (2001), Title, copyright and Table of Contents 18 pages.

Schraft, H. et al.; "Enumeration of heterotrophs, fecal coliforms and *Escherichia coli* in water: comparison of 3M™ Petrifilm™ plates with standard plating procedures", Journal of Microbiological Methods, vol. 60, 2005; pp. 335-342.

Food and Drug Administration Bacteriological Analytical Manual ("BAM"), 8th Ed., Revision A, (1998), AOAC International, Gaithersburg, MD, Title, copyright and Table of Contents 4 pages.

"Standard Methods for the Examination of Dairy Products", 17th Edition, Edited by H. M. Wehr et al.; The American Public Health Association, Washington, D.C., 2004, Title, copyright and Table of Contents 6 pages.

"Standard Methods of the Examination of Water and Wastewater," 20$^{th}$ Edition; Edited by L. S. Clesceria et al.; American Public Health Association; 1998, Title, copyright and Table of Contents 23 pages.

"AOAC Official Method 991.14 Coliform and *Escherichia coli* Counts in Foods—Dry Rehydratable Film (Petrifilm™ *E. coli*/ Coliform Count Plate™ and Petrifilm™ Coliform Count Plate™) Methods", Official Methods of Analysis of AOAC International, 18th Edition, 2005. Current throught Revision 4, 2011, AOAC International, Gaithersburg, MD, Title, copyright and method 3 pages.

ISO 9308-1. Water quality—Detection and enumeration of *Escherichia coli* and coliform bacteria—Part 1: Membrane filtration method, 2007, 24 pages.

Brochure entitled "3M Petrifilm™ Coliform Count Plate—Interpretation Guide"; #70-2008-4573-6 (1291.2) DPI: 1999; 6 pgs.

* cited by examiner

ENVIRONMENTAL SAMPLING ARTICLES AND METHODS

CROSS REFERENCE TO RELATED APPLICATION

This application is a divisional of application U.S. Ser. No. 12/743,528, filed Oct. 10, 2011 (now U.S. Pat. No. 8,828,653) which is a national stage filing under 35 U.S.C. 371 of PCT/US2008/084109, filed Nov. 20, 2008, which claims priority to U.S. Patent Application No. 60/989,356, filed Nov. 20, 2007, the disclosure of which is incorporated by reference in their entirety herein.

BACKGROUND

When surfaces become contaminated with bacteria, fungi, yeasts, viruses, or other microorganisms, or "microbes," sickness (morbidity) and, sometimes, death (mortality) may result. This is particularly true when surfaces in food processing plants and healthcare facilitates (e.g., hospitals) become contaminated with microorganisms.

In food processing plants, surfaces (e.g., solid surfaces, equipment surfaces, protective clothing, etc.) may become contaminated. Such contamination may be caused by or transferred to meat or other foods. In healthcare facilities, microbes may be released onto surfaces (e.g., solid surfaces, equipment surfaces, clothing, etc.) from infected individuals or otherwise. Once a surface becomes contaminated with microbes, contact with the contaminated surface may easily and readily transfer microbes to other locations, such as another surface, an individual, equipment, food, or the like.

As is well known, microbial contamination and transfer in certain environments may pose significant health risks. For example, the food that leaves a contaminated food processing plant will subsequently be eaten, and may cause sickness and, possibly, death. Microorganisms such as *Listeria monocytogenes*, *Salmonella enteritidis*, and *Escherichia coli* O157:H7 are of particular concern.

Microbial contamination is of concern in healthcare facilities since some of the patients of such facilities often suffer from infections by pathogenic microbes and, thus, bring the pathogenic microbes into such facilities. Further, many of those who are present in such facilities (e.g., patients) are sick and may be immunologically compromised. These individuals are, thus, at increased risk of becoming sick from infection by the contaminating microbes.

In view of the potential dangers of microbial contamination, in particular the ease with which microbes may be transferred in certain environments and the health hazards associated with the contamination of certain environments, a variety of techniques have been developed and employed to detect such contamination so that it may be promptly remedied.

Conventionally, environmental microbial testing includes obtaining a sample from a surface. This is typically done by contacting (e.g., wiping, swiping, etc.) the surface with a sterile sampling appliance, such as a swab or a sponge. Surfaces that are tested in this manner are usually quite clean; thus, the number of microorganisms that are picked up by the sampling appliance is typically quite low. Due to the small number of microorganisms, any microbes that are on (e.g., picked up by) the sampling appliance typically must be reproduced, or "grown" or "cultured," to provide a sufficient number of organisms for further analysis. Accordingly, at least a portion of the sample is then typically neutralized and, optionally, stabilized, repaired, or enriched, then applied (e.g., transferring, swiping, dipping and agitating, etc.) to an appropriate growth media (e.g., agar (a gelatin or gelatin-like material), broth (a liquid), etc.), which includes nutrients that will help microbes of interest grow. The growth media may be selective, meaning that the growth media may include ingredients that will allow some microorganisms to grow at faster rates than other microbes or it may include ingredients that will prevent the growth of at least some undesired microbes. The growth media is incubated or held at a certain temperature for a predetermined period of time, typically about 24 to about 48 hours, or until microbial growth is visibly apparent.

Once the sample has had a sufficient opportunity to grow, the amount of bacteria (e.g., the number of colonies on an agar plate) that has grown may then be evaluated (e.g., by an individual or with automated equipment) to provide some indication of the number and type of microbes that were present on a certain area of the surface at the time the sample was taken-usually a day or two earlier. Immunological or other testing may also be performed to determine or confirm the identity or identities of any microbes of interest that were present in the sample.

For example, when testing for a *Salmonella* species of bacteria, a sample potentially including the *Salmonella* species may be applied to a selective growth media. The selective growth media may then be incubated for a period of about 24 to about 48 hours until growth of *Salmonella* microbes is visible. Once *Salmonella* colonies are visibly present on the selective growth media, the colonies may be evaluated to confirm their identities, and, optionally, counted to estimate a number of *Salmonella* microorganisms present on a certain area of the tested surface. Alternatively or additionally, the cultured microorganisms may be subjected to an immunoassay or nucleic acid assay to more directly confirm their identities.

Simpler, rapid, accurate tests for environmental organisms are needed. This invention provides devices and methods for such tests.

SUMMARY

In one aspect, the invention includes an article for sampling and detecting surface microorganisms. The article can include a sample collector substantially free of hydrophilic agents and a reagent strip attached thereto. The sample collector can include a substrate with upper and lower major surfaces wherein at least one major surface is water-impervious and wherein at least one major surface comprises a porous material. The reagent strip can include a self-supporting substrate with upper and lower major surfaces wherein at least part of one major surface is coated with a cold water soluble gelling agent and a hydrophilic agent selected from the group consisting of a nutrient for growing microorganisms, a selective agent, a buffer, an indicator, and combinations of two or more of the foregoing. Optionally, the article may further include a barrier layer.

In another aspect, the invention includes an article for detecting or enumerating microorganisms. The article can include a bottom member and a cover sheet attached thereto. The bottom member can include a self-supporting water impervious substrate with upper and lower major surfaces wherein the upper major surface comprises an attachment structure. The cover sheet can include upper and lower major surfaces wherein at least part of the lower major surface of the cover sheet is coated with a cold water soluble powder including at least one gelling agent. The upper major surface of the bottom member faces the lower major surface of the cover sheet.

In another aspect, the invention includes a sample collector for collecting environmental surface samples. The sample collector can include a substrate with upper and lower major surfaces wherein at least one major surface is water impervious, wherein at least one major surface comprises a porous material, and wherein the sample collector is substantially free of hydrophilic agents.

In another aspect, the invention includes a sample housing comprising a bottom member, a spacer, a cover sheet, and a water-resistant barrier layer. The bottom member can include a self-supporting water-impervious substrate with upper and lower major surfaces. The spacer can include an aperture and is adhered to the upper surface of the bottom member. The cover sheet can include a substrate with upper and lower major surfaces wherein at least part of one major surface is coated with a cold water soluble powder including at least one gelling agent. The water-resistant barrier layer is positioned between the cover sheet and the spacer whereby a coated surface of the cover sheet faces the barrier layer.

In another aspect, the invention includes a reagent strip for the detection of microorganisms. The reagent strip includes a self-supporting substrate with upper and lower major surfaces and a dry coating on at least a part of both major surfaces. The coating can include a hydrophilic agent comprising a nutrient for growing microorganisms and an indicator and a cold water soluble gelling agent.

In another aspect, the invention includes a kit for sampling and detecting surface microorganisms. The kit can include a sample collector and a reagent strip. The sample collector is substantially free of hydrophilic agents and can include a water-impervious substrate with upper and lower major surfaces wherein at least one major surface comprises a porous material. The reagent strip can include a self-supporting substrate with upper and lower major surfaces wherein at least part of one major surface is coated with a cold water soluble gelling agent and a hydrophilic agent selected from the group consisting of a nutrient for growing microorganisms, a selective agent, a buffer, an indicator, and combinations of any two or more of the foregoing.

In another aspect, the invention includes a kit for sampling and enumerating microorganisms. The kit can include a sample collector, a sample housing and, optionally, a reagent strip. The sample collector can include a substrate with upper and lower major surfaces wherein at least one major surface is water-impervious. The sample housing can include a bottom member and a cover sheet. The bottom member can include a self-supporting water impervious substrate with upper and lower major surfaces. The cover sheet can include a substrate with upper and lower major surfaces wherein at least part of one major surface is coated with a cold water soluble powder including at least one gelling agent.

In another aspect, the invention includes a kit for sampling and enumerating microorganisms. The kit can include a sample collector, a cover sheet, and a bottom member. The sample collector consists essentially of a substrate with upper and lower major surfaces wherein at least one major surface is water-impervious. The cover sheet can include a substrate with upper surface and lower major surfaces wherein at least part of one major surface is coated with a cold water soluble powder including at least one gelling agent. The bottom member can include a self-supporting water-impervious substrate with upper and lower surfaces and an attachment structure.

In another aspect, the invention includes a method for detecting microorganisms on an environmental surface. The method can include providing a liquid sample-suspending medium, sample collector, a sample housing, and a reagent strip. The sample collector can include a substrate with upper and lower major surfaces wherein at least one major surface is water-impervious. The sample housing can include a bottom member and a cover sheet comprising a substrate with upper and lower major surfaces wherein at least part of one major surface of the cover sheet is coated with a cold water soluble powder including at least one gelling agent. The reagent strip can include a self-supporting substrate with upper and lower major surfaces wherein at least part of one major surface is coated with a cold water soluble gelling agent and a hydrophilic agent selected from the group consisting of a nutrient for growing microorganisms, a selective agent, a buffer, an indicator, and combinations of any two or more of the foregoing. The method further can include obtaining a sample on at least one major surface of the sample collector, forming an assembly by placing the sample-collector into the sample housing with the at least one major surface comprising the sample oriented toward the cover sheet, applying the sample-suspending medium to the sample collector major surface comprising the sample, contacting the lower surface of the cover sheet with the sample-suspending medium to form a hydrated gel, placing a coated surface of the reagent strip in contact with the hydrated gel, incubating the assembly for a period of time, and observing an indicator of microbial growth.

In another aspect, the invention includes a method for detecting microorganisms on an environmental surface. The method can include providing barrier layer, a sample-suspending medium, a sample collector, a sample housing, and a reagent strip. The sample collector can include a substrate with upper and lower major surfaces wherein at least one major surface is water-impervious. The sample housing can include a bottom member comprising a self-supporting water impervious substrate with upper and lower major surfaces and a cover sheet comprising a substrate with upper and lower major surfaces wherein at least part of one major surface is coated with a cold water soluble powder including at least one gelling agent. The method further can include obtaining a sample on at least one major surface of the sample collector, forming an assembly by placing the sample-collector into the sample housing with the at least one major surface comprising the sample oriented toward the cover sheet, applying the sample-suspending medium to the sample collector major surface comprising the sample, incubating the sample housing for a period of time, removing at least a portion of the barrier layer from the sample housing, contacting the lower surface of the cover sheet with the sample-suspending medium to form a hydrated gel, placing a coated surface of the reagent strip in contact with the hydrated gel, incubating the assembly for a period of time, and observing an indicator of microbial growth.

In another aspect, the invention provides a method of detecting *Listeria* species in an environmental sample. The method can include providing a sample collector with a surface, a sample suspending medium and a reagent strip; obtaining a sample on the surface of the sample collector; hydrating the sample or the reagent strip; and contacting the reagent strip and the sample. The reagent strip includes a dry coating that can include a hydrophilic agent comprising a nutrient for growing microorganisms, an indicator; and a cold water soluble gelling agent.

In another aspect, the invention provides a method of detecting *Listeria* species in an environmental sample. The method can include providing a sample collector with a surface, a sample suspending medium, a sample housing, and a reagent strip; obtaining a sample on the surface of the sample collector; placing the sample collector into the sample housing; hydrating the sample or the reagent strip; and contacting the reagent strip and the sample. The reagent strip can include a dry coating that includes a hydrophilic agent comprising a nutrient for growing microorganisms, an indicator; and a cold water soluble gelling agent.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a sample housing that comprises "a" barrier layer can be interpreted to mean that the sample housing can include "one or more" barrier layers.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further explained with reference to the drawing figures listed below, where like structure is referenced by like numerals throughout the several views.

DETAILED DESCRIPTION

The present disclosure provides articles and methods for sampling surfaces, temporarily storing the sample, and growing and detecting microorganisms present in the sample. As discussed in detail below, the inventive devices include the individual elements of a sample collector, a sample housing, a reagent strip, a barrier layer, combinations of two or more of the foregoing elements, and methods of using such devices. The present disclosure also includes kits for sampling surfaces and detecting microorganisms and methods of using such kits. Some traditional surface microbial sampling procedures involve an enrichment culture procedure, after which a fraction of the enrichment culture is tested for target microorganisms using subsequent biochemical, immunological, or genetic test procedures. Other traditional surface microbial sampling procedures use a moistened sponge or swab to wipe the surface. The sponge is subsequently extracted with neutralizing buffer or growth media and the portion of the target microorganisms that can be extracted from the sponge or swab is tested for the presence of target microorganisms. In contrast, the devices and methods of the present disclosure provide means to test the entire original sample collector and, thereby, are more likely to detect the presence of very low numbers of microorganisms on a surface. Furthermore, the devices and methods of the present disclosure are simpler and more convenient than traditional methods for detecting organisms in a surface sample.

Devices of the present disclosure provide a marked improvement over prior art devices and techniques which rely on standard agar plating methods as well as other microbiological testing. The media coated on the devices of the present invention do not contain matrixes which would adversely affect one's ability to visualize and isolate bacterial colonies. Not only will the media provided by the methods and devices allow enumeration of the bacterial colonies growing in the devices, but the colonies may be easily isolated for further testing in the same manner as bacterial colonies growing on conventional agar medium in a petri dish. The devices have the added feature of being much more compact and light-weight than petri dishes and take up less space in the laboratory. Furthermore, the devices are completely disposable allowing for safer and more rapid clean-up after use.

Sample Collector

Figure 1:
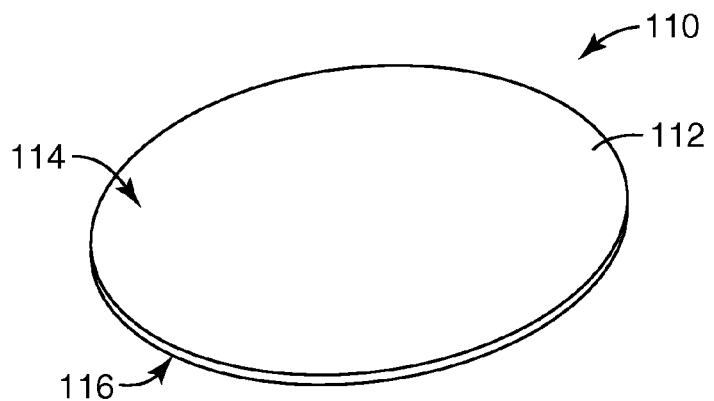
FIG. 1 is a perspective view of an exemplary embodiment of a sample collector according to the present invention.

FIG. 1 illustrates one embodiment of a sample collector 110 having a relatively smooth substrate 112 for sampling an environmental surface or patient surface. The substrate 112 has an upper major surface 114 and a lower major surface 116. At least one of the major surfaces of the substrate 112 is water impervious and/or may comprise a water-impervious coating. In some embodiments, the sample collector 110 is relatively flexible, allowing it to conform to and maintain contact with uneven surfaces. At least one of the major surfaces of the sample collector 110 is brought into contact with the sample area to effect transfer of material, such as liquids, solids, semi-solids, or combinations thereof, from the sample area to the sample collector 110. The sample collector 110 may be used to collect material from a sample area, such as a food contact surface or a superficial wound, which is to be analyzed.

The substrate 112 of the sample collector 110 may be constructed from various materials. Nonlimiting examples of suitable materials for include plastic films, such as polyethylene, polypropylene, or polyester; cellulosic materials, such as paper or cardboard, which comprise a coating or a composition to render at least one major surface water-impervious; foams, such as polyethylene or polystyrene foam; or fabrics which have at least one major surface that is water-impervious.

Figure 2A:
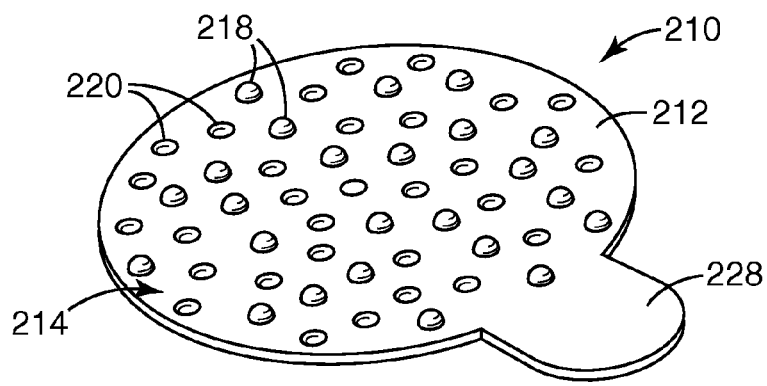
FIG. 2A is a top perspective view of an exemplary embodiment of a textured sample collector according to the present invention.

In some embodiments, at least one major surface of the sample collector 110 is textured. As used herein, the word "textured" refers to the profile of the surface that is used to collect the sample material. For example, the texture of the major surfaces of the sample collector 110 may be relatively smooth, as illustrated in FIG. 1. Alternatively, the texture of the major surfaces of the sample collector 110 may be relatively rough. FIG. 2A illustrates one embodiment of a sample collector 210 including a major surface 214 with a relatively rough texture. In this embodiment, the substrate 212 may comprise a combination of raised structures 218 and recessed structures 220. Alternatively, the substrate 212 may comprise raised structures 218 or recessed structures 220. Raised structures 218 may be present in various sizes and may be present in various shapes, such as bumps, spikes, ridges, and the like, or combinations thereof. The raised structures 218 may be randomly distributed across the surface of the substrate 212 or, alternatively, may be uniformly spaced apart. Recessed structures 220 may be present in various sizes and may be present in various shapes, such as holes, pits, valleys, troughs, channels, microchannels, and the like, or combinations thereof. The raised structures 218 or recessed structures 220 may be an integral part of the substrate 212 material from which the sample collector 210 is made. Alternatively, the structures may be bonded to the substrate 212. Without being bound by theory, it is believed that a sample collector 210 comprising either raised structures 218 or recessed structures 220 may provide an advantage in collecting sample material from an environmental surface or a patient surface by providing structures that can trap sample material and/or abrade and collect material from the surface to be sampled. Also illustrated in FIG. 2A is an optional tab 228, which provides a convenient area to hold the sample collector 210 while collecting the sample.

Figure 2B:
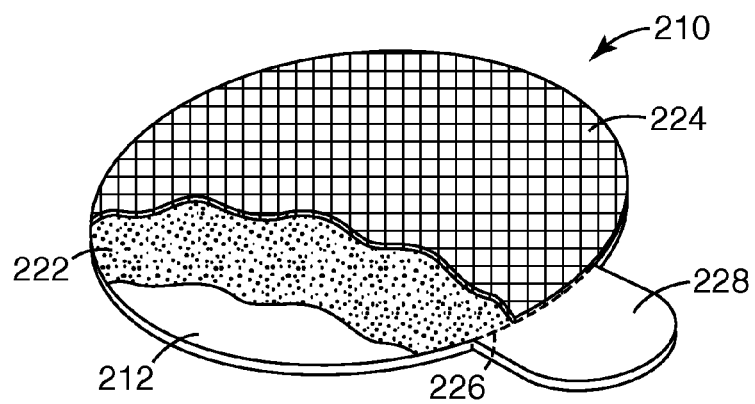
FIG. 2B is a perspective view of an exemplary embodiment of a sample collector comprising a porous material according to the present invention.

FIG. 2B illustrates a sample collector 210 with an alternative textured surface. The sample collector 210 can comprise a bonded material 224, such as a nonwoven, adhered to a major surface of the substrate 212 by means of an adhesive layer 222. Adhesive layer 222 may be water-insoluble, should be non-inhibitory to the growth of microorganisms, and should be capable of withstanding the sterilization process. Preferably, the adhesive layer 222 and the bonded material 224 are sufficiently transparent when wet to enable the viewing of bacterial colonies through the substrate 212 coated with the adhesive layer 222. In some embodiments, the adhesive layer 222 includes a pressure-sensitive adhesive. An exemplary embodiment of a bonded material 224 adhered to the substrate 212 includes a nonwoven material, such as a knitted loop nonwoven obtained from Gehring Textiles, Inc. (Garden City, N.Y.) or glass fiber filter, adhered to a plastic substrate 212, such as white polyester (5 mil (0.13 mm) thickness), by means of a pressure-sensitive adhesive layer 222, such as a tackified high pressure sensitive iso-octyl acrylate/acrylic acid copolymer adhesive (96 wt. % iso-octyl acrylate and 4 wt. % acrylic acid) Alternatively, the bonded material 224 may comprise other textured materials, such as foams (e.g., polyurethane foam), fabrics, or cellulosic materials (e.g. filter paper). Also shown in FIG. 2C is a tab 228, which is conveniently detachable from sample collector 210 by means of a perforation 226.

Sample Housing

The sample housing is an article into which a sample collector, with sample material disposed thereon, may be placed and, optionally, stored for a period of time. The sample housing further may be used as an article into which solutions and/or reagents may be added to facilitate the growth, detection, or enumeration of microorganisms. In certain embodiments, the sample housing may be used as an article in which a sample is incubated with a reagent strip and/or reagents to facilitate the growth, detection or enumeration of microorganisms.

Figure 3A:
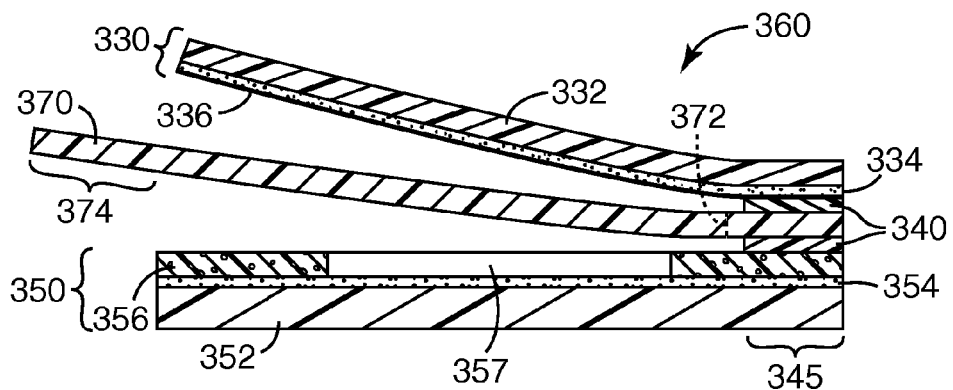
FIG. 3A is a cross-sectional schematic view of an exemplary embodiment of a sample housing comprising a spacer according to the present invention.

FIG. 3A illustrates an exemplary sample housing 360. The sample housing 360 comprises a bottom member 350, a barrier layer 370, and a cover sheet 330.

The bottom member 350 comprises a self-supporting water-impervious substrate 352 with upper and lower major surfaces. The bottom member 350 is preferably a relatively stiff material such as polyester, polypropylene or polystyrene film, which will not absorb or otherwise be affected by water. For example, polyester films approximately 0.004 to 0.007 inch (0.1-0.2 mm) thick, polypropylene films approximately 0.004 to 0.008 inch (0.1-0.2 mm) thick and polystyrene films approximately 0.015 inch (0.38 mm) thick should work well. Other suitable substrates include paper with a polyethylene or other water-proof coating. The bottom member 350 may be either transparent or opaque, depending on whether one wishes to view bacterial colonies through the bottom member 350. To facilitate the counting of bacterial colonies, the bottom member 350 may have a square grid pattern printed thereon as described in U.S. Pat. No. 4,565,783, which is incorporated herein by reference. The materials used to construct the bottom member 350 should be relatively inert to microorganisms and should be compatible with the sterilization process.

In this embodiment, the bottom member 350 is further comprised of an adhesive layer 354 disposed on the upper surface of the substrate 352 and a spacer 356. The adhesive layer 354 forms an attachment between the spacer 356 and the substrate 352. The adhesive layer 354 should be selected according to the guidelines for the adhesive layer 222 of the sample collector 210 described above. The spacer 356, which comprises an aperture 357, should be constructed from a water-insoluble material. The walls of the aperture 357 provide a well of predetermined size and shape to confine a volume of liquid medium added to the sample housing 360. The spacer 356 should be thick enough and the aperture 357 large enough to form a well of the desired volume, e.g., 1 milliliters, 2 milliliters, 3 milliliters, or 5 milliliters. Closed cell polyethylene foam or polystyrene foam are suitable materials for the spacer 356, but any material which is hydrophobic (non-wetting), inert to microorganisms, and, preferably, capable of withstanding a sterilization process may be used. As illustrated in FIG. 3A, the bottom of the well formed by the aperture 357 may comprise an adhesive layer 354, which may be used to secure a sample collector (not shown in FIG. 3A). Alternatively, the bottom of the well formed by the aperture 357 may comprise attachment structures (described below) or no adhesive layer 354 or attachment structures.

Attached to the upper surface of the spacer 356 is a barrier layer 370. In this embodiment, the spacer 356 and the barrier layer 370 are joined together by a double-sided adhesive tape 340. The barrier layer 370 should be water-resistant. Barrier layer 370 is preferably transparent to permit the observation of objects located beneath the barrier layer 370 and is substantially impermeable to bacteria, water and water vapor. Generally, the barrier layer 370 can have the same properties as bottom member 350, but need not be as stiff. Exemplary materials for barrier layer 370 include, for example, polypropylene film (e.g., 1.6 mil biaxially-oriented polypropylene (BOPP)) or polyethylene film. Referring back to FIG. 3A, the barrier layer 370 is shown with an optional perforation 372, which can be torn easily to permit the removal of at least a part of the barrier layer 370 from the sample housing 360. The barrier layer 370 also is shown with an optional extension, or tab 374, which allow the barrier layer 370 to be grasped easily to tear the perforation 372.

Attached to the upper surface of the barrier layer 370 is a cover sheet 330. The barrier layer 370 and the cover sheet 330 are joined together by a double-sided adhesive tape 340. The attachment of the spacer 356 to the barrier layer 370 and the cover sheet 330 near an edge of the sample housing 360 conveniently forms a hinge region 345 allowing the barrier layer 370 and/or the cover sheet 330 to be lifted, thus exposing inner portions of the sample housing 360 while retaining the alignment of the component parts. Certain low-adhesion adhesive mixtures, such as those described in U.S. Pat. No. 5,118,750, may be used on at least one side of the double-sided adhesive tape 340 to form a detachable attachment between the elements (e.g., cover sheet, barrier layer, and bottom member). The cover sheet 330 and barrier layer 370 may alternatively be joined to the bottom member 350 by other means, for example ultrasonic welding, clamping, or stapling.

The cover sheet 330 comprises a substrate 332 with upper and lower major surfaces. Coated on at least part of the lower major surface (facing the barrier layer 370) is an adhesive layer 334. A cold water soluble powder 336 including at least one gelling agent is adhered to the adhesive layer 334. Alternatively, at least a portion of the cover sheet 330, such as the hinge region 345, may be coated with only an adhesive or may be substantially free of any type of coating.

Adhesive layer 334 should be coated onto cover sheet 330 at a thickness which is preferably less than the diameter of the particles of the powdered gelling agent and/or nutrients. The object is to apply enough adhesive in adhesive layer 334 to adhere the particles to the substrate but not so much that the particles become completely embedded in the adhesive. A uniform monolayer of powder 336 is desired with sufficient surface area exposed for hydration. Generally, an adhesive layer 334 in the thickness range of 0.0002 to 0.0005 inch (0.005-0.012 mm) is suitable. An exemplary adhesive used in adhesive layer 334 is a copolymer of isooctylacrylate/acrylamide (in a mole ratio of 94/6). Other pressure sensitive adhesives which may be used include isooctylacrylate/acrylic acid (in a mole ratio of 95/5 or 94/6) and silicone rubber. Adhesives which turn milky upon exposure to water are less preferred, but may be used in conjunction with a non-transparent substrate or where colony visualization is not required.

A monolayer of cold-water-soluble powder 336 is adhered uniformly to adhesive layer 334. Powder 336 may comprise a gelling agent or a mixture of gelling agents. As used in the specification and claims, the term "powder" designates a finely divided particulate material having an average diameter of less than 400 micrometers. As used in the specification and claims, the term "cold-water-soluble" designates material which forms a solution in water at room temperature. Suitable gelling agents for inclusion in powder 336 include both natural and synthetic gelling agents which form solutions in water at room temperature. Gelling agents such as hydroxyethyl cellulose, carboxymethyl cellulose, polyacrylamide, locust bean gum and algin, form solutions in water at room temperature and are suitable gelling agents for providing powders which are "cold-water-soluble." The preferred gelling agents for powder 336 are guar gum and xanthan gum, these gelling agents being useful individually or in combination with one another.

The gelling agent is preferably present in an amount sufficient to form a substantially transparent gel having a Brookfield viscosity of at least 1500 cps. A sufficient amount of the gelling agent should be adhered to the cover sheet 330 so that a predetermined quantity of water or an aqueous sample, e.g., 1-3 milliliters, placed in the sample housing 360 will form a gel having a viscosity of about 1500 cps or more when measured at 60 rpm with a Brookfield Model LVF viscometer at 25° C. Gels of this viscosity will allow convenient handling and stacking and provide distinct colony identification. In most cases 0.025 to 0.050 gram of guar gum on a surface area of 3.14 $in^2$ (5.07 $cm^2$) will provide a sufficiently viscous gel when hydrated with 1-3 milliliters of an aqueous sample. The size of the particles of powder 336 may be used to control the coating weight per unit area. For example, approximately 100 mesh guar gum coats to a weight of about 0.05 grams/2-inch (5.1 cm) diameter disc; and a 400 mesh guar gum coats to a weight of about 0.025 grams/2-inch (5.1 cm) diameter disc.

The cover sheet 330 provides a means for covering the sample housing 360 to prevent contamination during sample storage and/or incubation. The cover sheet 330 can be a water-resistant sheet attached, directly or indirectly, in hinge region-like fashion to one edge of the bottom member 350. Cover sheet 330 is preferably transparent to facilitate counting of the bacterial colonies and is substantially impermeable to bacteria and water vapor. As used herein, "substantially impermeable to bacteria and moisture vapor" designates a cover sheet 330 which prevents undesired contamination of the sample housing 360 during shipping, storage and use of the devices and which provide an environment which will support the growth of microorganisms during the incubation period. Generally, it can have the same properties as bottom member 350, but need not be as stiff. Cover sheet 330 can be selected to provide the amount of oxygen transmission necessary for the type of microorganism desired to be grown. For example, polyester films have low oxygen permeability (less than 5 g/100 $in^2$ (645 $cm^2$)/24 hours per 0.001 inch (0.025 mm) of thickness) and would be suitable for growing anaerobic bacteria. On the other hand, polyethylene has very high oxygen permeability (approximately 500 g/100 $in^2$ (645 $cm^2$)/24 hours per 0.001 inch (0.025 mm) of thickness) and would be suitable for aerobic organisms. A preferred material for cover sheet 330 is a 1.6 mil biaxially-oriented polypropylene film.

The cover sheet 330 simply can be lifted, a liquid sample-suspending medium can be placed on the substrate, and the cover sheet 330 then can be returned to its original position thereby sealing in the gelled medium. The cover sheet 330 is preferably transparent to allow the bacterial colonies to be seen. The materials used to form the cover sheet 330 may be conveniently selected to obtain the desired permeability to gases such as oxygen.

Figure 3B:
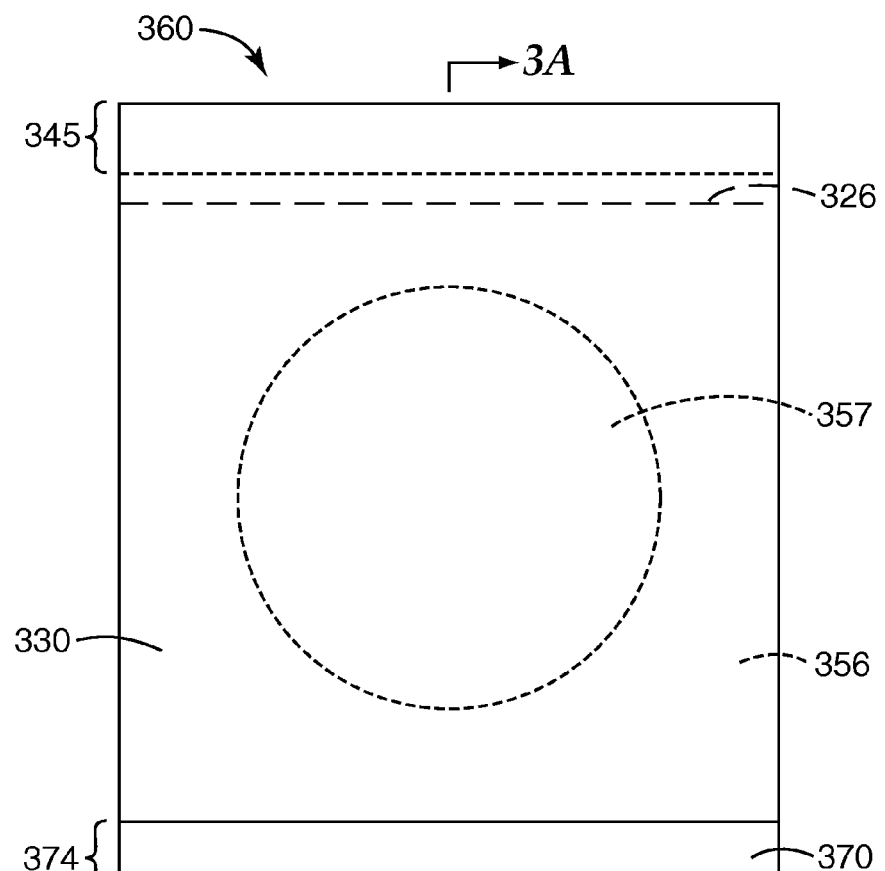
FIG. 3B is a plan view of the sample housing of FIG. 3A.

FIG. 3B shows a top view of the sample housing 360 of FIG. 3A. The hinge region 345 is located along the top edge of the sample housing 360. The optional perforation 372 is adjacent to the hinge region 345. The circular aperture 357 in the spacer 356 is located in the central region of the sample housing 360. The tab 374 of the barrier layer 370 can be seen extending beyond the edge of the cover sheet 330 at the end of the sample housing 360 opposite the hinge region 345.

Figure 4:
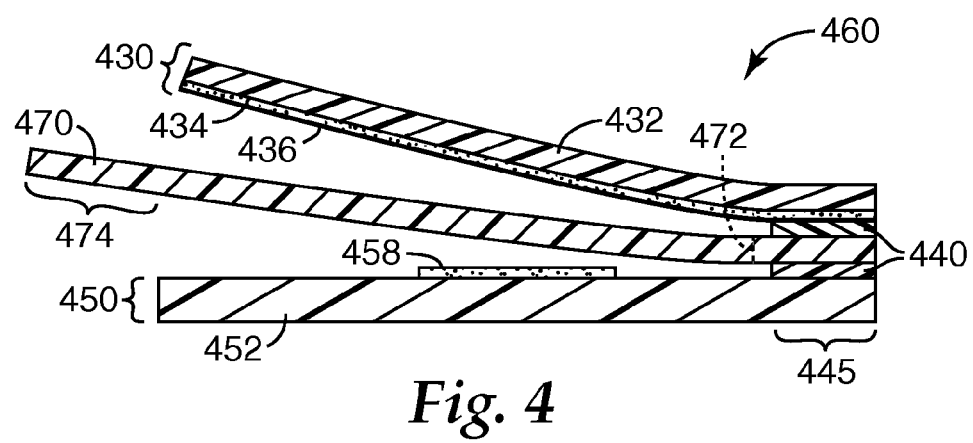
FIG. 4 is a cross-sectional schematic view of one embodiment of an article for sample collection and enumeration of microorganisms.

FIG. 4 illustrates an alternative embodiment of a sample housing 460. The sample housing 460 is comprised of cover sheet 430, barrier layer 470, and bottom member 450 elements, secured at a hinge region 445 by, for example, double-sided adhesive tape 440. In this embodiment, the bottom member 450 comprises a substrate 452 and an optional attachment structure 458. The attachment structure 458 may comprise an adhesive, a component of a hook-and-loop attachment means, a stem web structure such as those described in U.S. Patent Application Publication No. 2003/0088946A, or the like, which can be used to hold a sample collector in place. The barrier layer 470 may comprise a perforation 472 and/or a tab 474 and can be constructed as described above. In certain embodiments, the lower major surface of the barrier layer 470 may comprise a release material, to prevent adhesion to the attachment structure 458. Release coatings are known in the art and are routinely used to reduce the adhesion between adhesives and plastic films. The cover sheet 430 comprises a substrate 432, adhesive layer 434, and powder 436 and can be constructed as described above.

Reagent Strip

Figure 5:
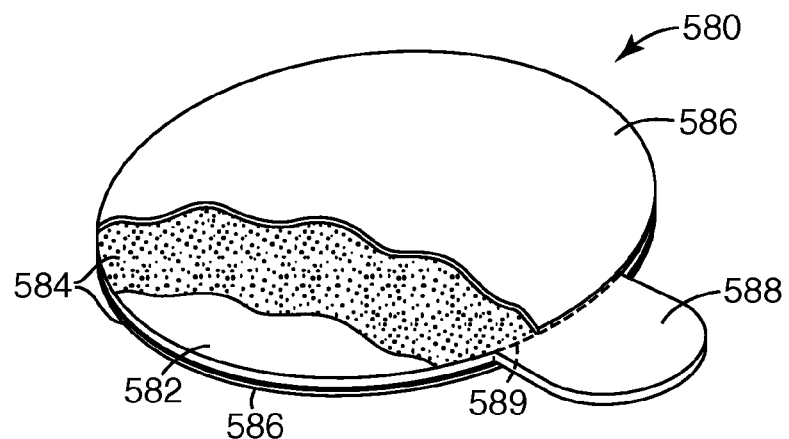
FIG. 5 is a perspective schematic view of one embodiment of a reagent strip according to the present invention.

FIG. 5 illustrates one embodiment of a reagent strip 580 according to the present invention. The reagent strip 580 is comprised of a substrate 582 with upper and lower major surfaces. In this embodiment, at least a part of both major surfaces of the substrate 582 is coated with an optional adhesive 584 and a hydrophilic agent 586. In some embodiments, at least a part of one major surface of the substrate 582 is coated with the optional adhesive 584 and/or the hydrophilic agent 586. In some embodiments, the reagent strip 580 comprises an optional tab 588. The tab may include an optional perforation 589, which allows the tab 588 to be separated from the reagent strip 580.

The detection of microorganisms in a sample often involves the use of reagents, such as hydrophilic agents, to promote growth, inhibit growth, and/or detect a metabolic activity of certain microorganisms. "Hydrophilic agents", as used herein, include nutrients (e.g., proteins, peptides, carbohydrates, vitamins) at concentrations which may be used to promote the growth of certain microorganisms, salts (e.g., NaCl, LiCl, potassium tellurite) or inhibitors (e.g. nalidixic acid, aztreonam, other antibiotics, dyes) at concentrations which may be used to selectively inhibit the growth of certain microorganisms, dyes or indicators (e.g. triphenyltetrazolium chloride, chlorophenol red, bromthymol blue, o-nitrophenylphosphate, 5-bromo-4-chloro-3-indolyl-β-glucopyranoside) at noninhibitory concentrations which may be used to detect metabolic activity such an enzyme activity or a fermentation process, and gelling agents (e.g., agar, xanthan gum, guar gum).

The adhesive 584 may be required when coating certain hydrophilic agents 586, such as powders, onto the substrate 582, as discussed above. In some embodiments, the hydrophilic agent 586 comprises a gelling agent which, when hydrated to form a gel, may be coated directly onto the substrate 582. The substrate 582 may be selected from a number of materials, such as the materials described above for the construction of bottom member, the barrier layer, and the cover sheet. In certain embodiments, the substrate 582 of the reagent strip 580 is free-standing. In certain embodiments, the substrate 582 of the reagent strip 580 may be substantially impervious to water. In alternative embodiments, the substrate 582 of the reagent strip 580 may be water-absorbent, such as a filter paper or a hydrophilic foam. In certain embodiments, the reagent strip 580 may be constructed from polyethylene-coated paper and may comprise an optional printed grid (not shown) to facilitate counting colonies of microorganisms.

It may be desirable to incorporate a dye into the hydrophilic agents 586 included on the reagent strip 580. The dye may be incorporated into a gel or powder mixture coated on the substrate 582. Alternatively, the dye may be incorporated into the adhesive 584. Suitable dyes are those which are metabolized by the growing microorganisms, and which cause the colonies to be colored for easier visualization. Examples of such dyes include triphenyltetrazolium chloride, p-tolyl tetrazolium red, tetrazolium violet, veratryl tetrazolium blue and related dyes. Other suitable dyes are those sensitive to pH changes such as neutral red or chlorophenol red.

The material employed in the hydrophilic agent 586 on the reagent strip 580 is cold-water-reconstitutable. As used herein, "cold-water-reconstitutable" designates material which forms a solution, sol or gel in water at room temperature. Suitable gelling agents for inclusion in the coating of this embodiment (if such are contained in the coating) include the above-described gelling agents, such as guar gum and locust bean gum, which form solutions in water at room temperatures.

The reagent strip may be used to select for the growth of certain organisms, such as members of the genus *Listeria*. In these embodiments, the hydrophilic agents may include a combination of nutrients and selective inhibitors that favor the growth of *Listeria* species over other microorganisms that may be present in a surface sample. For example, the reagent strip may include a pancreatic digest of casein, a proteose peptone such as proteose peptone #3, yeast extract, a buffering system such as disodium phosphate and monopotassium phosphate, sodium chloride, lithium chloride, nalidixic acid, acriflavin, moxalactam, and polymyxin B sulfate in concentrations that are effective to support the growth of *Listeria* species and/or inhibit the growth non-*Listeria* species. The reagent strip may further include an indicator system, such as a chromogenic enzyme substrate (e.g., 6-Chloro-3-indoxyl-α-D-mannopyranoside) and, optionally, a corresponding enzyme inducer (e.g., 1-O-methyl-α-D-mannopyranoside) at effective concentrations to detect the presence of *Listeria* species in the sample.

Microbial Detection or Enumeration Articles

The present invention includes articles used to detect and/or enumerate microorganisms in a surface sample. Such articles, which include the previously-described sample housings, comprise various combinations of elements (e.g., cover sheet, sample collector, barrier layer, bottom member) described above.

Figure 6:
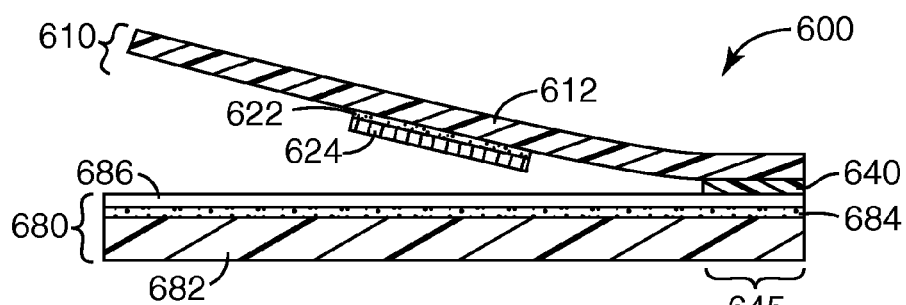
FIG. 6 is a cross-sectional schematic view of an alternative embodiment of an article for sample collection and enumeration of microorganisms.

FIG. 6 illustrates one embodiment of an article 600 for sample collection and microbial enumeration. The article 600 is comprised of sample collector 610 and reagent strip 680 elements, constructed as described above. The sample collector 610 comprises a water-impervious substrate 612 and a bonded material 624. The bonded material 624 is attached to the lower major surface of substrate 612 by an adhesive 622. In this embodiment, the reagent strip 680 comprises a self-supporting substrate 682 with upper and lower surfaces, at least a part of one major surface coated with a hydrophilic agent 686. Also shown in FIG. 6 is the optional adhesive 684. The sample collector 610 and reagent strip 680 are attached in this embodiment by a double-sided adhesive tape 640 at the hinge region 645. Certain low-adhesion adhesive mixtures, such as those described in U.S. Pat. No. 5,118,750, may be used on at least one side of the double-sided adhesive tape 640 to form a detachable (and re-attachable) attachment between the sample collector 610 and reagent strip 680.

Preferably, the sample collector 610 and reagent strip 680 are attached near one edge of the article 600, forming a hinge region 645. A skilled person will recognize other suitable ways to form the hinge region 645, such as adhesives, heat-bonding, ultrasonic welding, and the like. It is also contemplated that the sample collector 610 and reagent strip 680 may be formed from a single piece of water-impervious material, with a hinge region 645 formed by folding the material back on itself (not shown).

Figure 7:
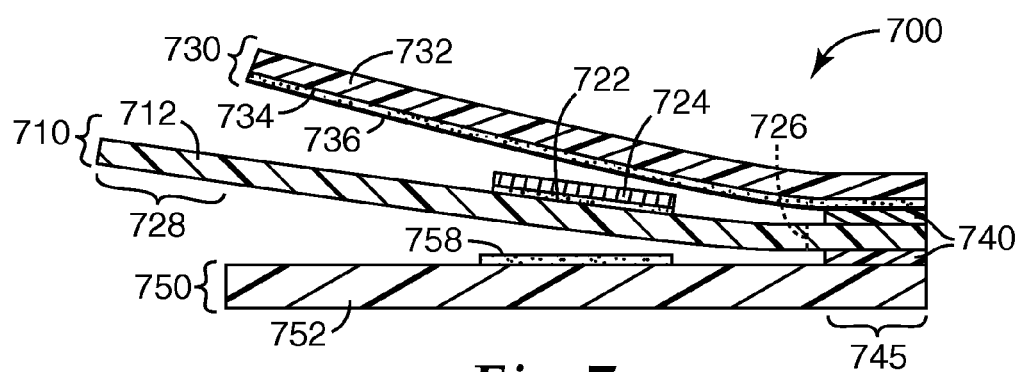
FIG. 7 is a cross-sectional schematic view of an alternative embodiment of an article for sample collection and enumeration of microorganisms.

FIG. 7 illustrates an alternative embodiment of an article 700 for sample collection and microbial enumeration. The article 700 is comprised of sample collector 710, cover sheet 730, and bottom member 750 elements, the elements constructed as described above. The cover sheet 730 is comprised of a substrate 732, an adhesive layer 734, and powder 736. The sample collector 710 can be attached to the cover sheet 730 via a double-sided adhesive tape 740. The sample collector 710 includes a bonded material 724, for sample collection, attached to the substrate 712 by an adhesive layer 722. In this embodiment, the sample collector 710 includes a perforation 726 near the hinge region 745, for easy removal of the sample collector 710 from the article 700. The sample collector also includes a tab 728 to grasp the sample collector 710 during handling. A bottom member 750 is attached to the sample collector 710 via a double-sided adhesive tape 740. The bottom member 750 comprises a substrate 752 and an optional attachment structure 758, to which the sample collector 710 can be affixed. The attachment structure 758 may comprise an adhesive, a component of a hook-and-loop attachment means, or the like, which can be used to hold a sample collector 710 in place. In certain embodiments, the sample collector 710 major surface that faces the attachment structure 758 may comprise a release material, to control adhesion of the sample collector 710 to the attachment structure 758, when said attachment structure 758 comprises an adhesive. Release coatings are known in the art and are routinely used to reduce the adhesion between adhesives and plastic films.

Figure 8:
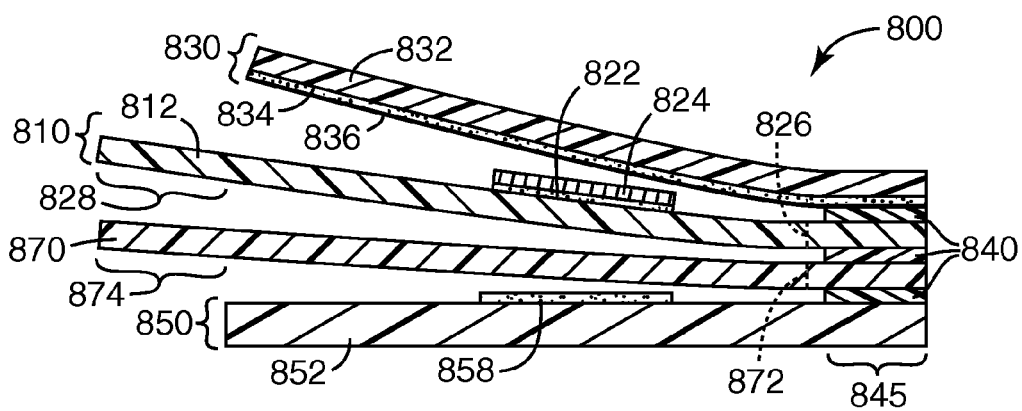
FIG. 8 is a cross-sectional schematic view of an alternative embodiment of an article for sample collection and enumeration of microorganisms.

FIG. 8 illustrates an alternative embodiment of an article 800 for sample collection and microbial enumeration. The article 800 is comprised of cover sheet 830, barrier layer 870, sample collector 810, and bottom member 850 elements, the elements constructed as described above. The cover sheet 830 is comprised of a substrate 832, an adhesive layer 834, and powder 836. The sample collector 810 can be attached to the cover sheet 830 via a double-sided adhesive tape 840. The sample collector 810 includes a bonded material 824, for sample collection, attached to the substrate 812 by an adhesive layer 822. In this embodiment, the sample collector 810 includes a perforation 826 near the hinge region 845, for easy removal of the sample collector 810 from the article 800. The sample collector also includes a tab 828 to grasp the sample collector 810 during handling. A barrier layer 870 is attached to the sample collector 810 via a double-sided adhesive tape 840. The barrier layer 870 also includes a perforation 872 near the hinge region 845 and a tab 874 to grasp the barrier layer 870 during handling. A bottom member 850 is attached to the barrier layer 870 via a double-sided adhesive tape 840. The bottom member 850 comprises a substrate 852 and an optional attachment structure 858, to which the sample collector 810 can be affixed. The attachment structure 858 may comprise an adhesive, a component of a hook-and-loop attachment means, or the like, which can be used to hold a sample collector 810 in place. In certain embodiments, the barrier layer 870 major surface that faces the attachment structure 858 may comprise a release material, to control adhesion of the sample collector 810 to the attachment structure 858, when said attachment structure 858 comprises an adhesive. Release coatings are known in the art and are routinely used to reduce the adhesion between adhesives and plastic films.

Samples and Microorganisms

One aspect of the present invention is that it may be used to detect organisms present on a wide variety of surfaces. The devices and methods of the present invention may be used for a variety of applications where it is desirable to test the organisms present on a surface, including, but not limited to, food surfaces (e.g. beef carcasses, exterior surfaces of produce), food processing surfaces, water or water film surfaces, patient surfaces, patient treatment surfaces, hospital environmental surfaces, clinic environmental surfaces, and forensic environmental surfaces. The samples may consist substantially of solid, semi-solid, gelatinous, or liquid material, alone or in various combinations. The apparatus and system of the invention, as well as the inventive methods, may be used to determine, qualitatively or quantitatively, the presence of one or more microorganisms of interest.

An exemplary clinical analyte of interest to detect is *Staphylococcus aureus* ("*S. aureus*"). This is a pathogen causing a wide spectrum of infections including: superficial lesions such as small skin abscesses and wound infections; systemic and life threatening conditions such as endocarditis, pneumonia and septicemia; as well as toxinoses such as food poisoning and toxic shock syndrome. Some strains (e.g., Methicillin-Resistant *S. aureus* or MRSA) are resistant to all but a few select antibiotics.

Exemplary analytes of interest to detect in food processing areas are members of the genus *Listeria*. *Listeria* are classified as gram-positive, rod-shaped bacteria and consist of the species *Listeria monocytogenes*, *L. innocua*, *L. welshimeri*, *L. seeligeri*, *L. ivanovii*, and *L. grayi*. Among these, *L. monocytogenes* is responsible for the majority of human listeriosis cases and immunocompromised, pregnant women, elderly, and newborns have increased susceptibility to infection. The most common symptoms of listeriosis are septicemia, meningitis, and miscarriages.

Other microorganisms of particular interest for analytical purposes include prokaryotic and eukaryotic organisms, particularly Gram positive bacteria, Gram negative bacteria, fungi, *mycoplasma*, and yeast. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Vibrio* spp., *Clostridium* spp., *Corynebacteria* spp. as well as, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis*, *Streptococcus pneumoniae*, *S. agalactiae*, *S. pyogenes*, *Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis*, *Pseudomonas aeruginosa*, *Escherichia coli*, *Aspergillus niger*, *A. fumigatus*, *A. clava-*

*tus, Fusarium solani, F. oxysporum, F. chlamydosporum, Vibrio cholera, V. parahaemolyticus, Salmonella choleraesuis, S. typhi, S. typhimurium, Candida albicans, C. glabrata, C. krusei, Enterobacter sakazakii, Escherichia. coli* O157, ESBL-containing microorganisms, and multiple drug resistant Gram negative rods (MDR).

Articles of Manufacture

Sample housings and/or articles of the invention can be combined with packaging material and sold as a kit for sampling and detecting microorganisms on surfaces. For example, the kits may comprise two or more components (e.g., bottom member, spacer, barrier layer, cover sheet and/or reagent strip; each component as described above) packaged together. In some embodiments, two or more of the components (e.g. bottom member, barrier layer, and cover sheet) may be provided attached to each other, preferably forming a hinge region, as shown in the illustrated embodiments. In these embodiments, certain components (e.g., the sample collector, reagent strip, and/or the barrier layer) may be detachable. In other embodiments, the components may be provided separately and can be assembled during use. The kits may further comprise sampling and testing accessories, such as a sample suspending medium, a pipette, a label, a sample carrier, or a glove.

Environmental Sampling and Detection Methods

The present disclosure includes methods for detecting microorganisms on an environmental surface. The methods may be used to detect the presence or absence of a target microorganism by observing an indicator of microbial growth of the target microorganism. The methods further may be used to enumerate microorganisms in a sample. The elements that are used in these methods (e.g. sample collector, cover sheet, barrier layer, etc.) may be provided separately or may be parts of an assembly, such as the sample housings described above. Furthermore, the individual elements and/or assemblies may be provided in a kit, as described above. The embodiments described herein.

In one embodiment, the method comprises providing a liquid sample suspending medium; a sample collector such as sample collector 210 (FIG. 2B), a sample housing such as sample housing 460 (FIG. 4) comprising a bottom member 450 and cover sheet 430, and a reagent strip such as reagent strip 580 (FIG. 5). The method further comprises contacting one of the major surfaces, such as a bonded material 224, of the sample collector 210 with the surface or material to be tested. Typically, the operator may use sterile forceps, or the like, or may use a gloved hand to hold the sample collector 210 while the sample is collected. The sample collector 210 is brought into physical contact (e.g., touching, wiping, or rubbing) with a prescribed surface area, such as 5 cm by 5 cm, 10 cm by 10 cm or 25 cm by 25 cm, in order to estimate the number of organisms in an area of known dimensions. In this embodiment, the barrier layer 470 is lifted away from the bottom member 450 and the sample collector 210 is placed in contact with the attachment structure 458 with the sample oriented toward the barrier layer 470. The method further comprises applying the sample suspending medium to the bonded material 224 of the sample collector 210 comprising the sample. The sample suspending medium may be applied using a pipette or by other suitable means. After adding the sample suspending medium, the barrier layer 470 may be lowered. Optionally, the sample may be incubated for a period of time, such as at least 30 minutes, at least 60 minutes, or at least 120 minutes, depending upon the target microorganism, to allow the recovery of injured microorganisms. The incubation temperature may be chosen according to the target microorganism. After the optional incubation period, the cover sheet 430 is lifted and the barrier layer 470 is removed, for example by separating the barrier layer 470 at the perforation 472. The method further comprises contacting the lower surface of the cover sheet 430 with the sample suspending medium to form a hydrated gel. This may be accomplished, for example, by grasping the cover sheet 430 with one hand, grasping the bottom member 450 with the other hand, and lifting the cover sheet 430. Although the hydrated gel forms within seconds, it is preferable to allow the gel to form for at least 5-10 minutes, more preferably, at least 10-30 minutes before opening the device to expose the hydrated gel. The gel may remain attached to the cover sheet 430, the gel may remain attached to the sample collector 210, or separate portions of the gel may remain attached to the cover sheet 430 and to the sample collector 210. Optionally, the method further comprises placing a coated surface of the reagent strip 580 in contact with the hydrated gel. While the cover sheet 430 is raised, a reagent strip 580 may be inserted into the sample housing 460, with the hydrophilic agent 586 of the reagent strip 580 oriented toward the gel. The sample housing 460 is incubated for a period of time to allow the number of microorganisms present in the sample to increase and/or to allow the metabolic activity of the microorganisms to cause a detectable change in an indicator. The device is typically incubated at temperatures from 25-45° C., preferably 25-37° C. In certain embodiments, the microorganisms form discrete colonies in the hydrated gel. The number of microorganisms in the original sample may be enumerated by counting colonies.

In another embodiment, the method comprises providing a liquid sample suspending medium; any sample collector (see, for example, FIGS. 1. 2A-B); a sample housing such as sample housing 360 (FIG. 3A) comprising a bottom member 350, a barrier layer 370, and a cover sheet 330; and a reagent strip such as the reagent strip 580 (FIG. 5). The method further comprises contacting one of the major surfaces of the substrate or bonded material of the sample collector with the surface or material to be tested, as described above. The sample collector can be placed into the sample housing 360 with the sample oriented toward the barrier layer 370. In this embodiment, the barrier layer 370 can be lifted and the sample collector can be placed into the well formed by aperture 357 with the sample oriented upward (toward the barrier layer 370). In some embodiments, the sample collector may be sized and shaped so that it fits completely inside the well formed by aperture 357. The method further comprises dispensing the sample suspending medium into the well containing the sample collector. The sample suspending medium may be dispensed using a pipette or by other suitable means. After adding the sample suspending medium, the barrier layer 370 may be lowered. Optionally, the sample may be incubated for a period of time, such as at least 30 minutes, at least 60 minutes, or at least 120 minutes, depending upon the target microorganism, to allow the recovery of injured microorganisms. After the optional incubation period, the cover sheet 330 is lifted and the barrier layer 370 is removed, for example by separating the barrier layer 370 at the perforation 372. The method further comprises contacting the lower surface of the cover sheet 330 with the sample suspending medium to form a hydrated gel, as described above. Although the hydrated gel forms within seconds, it is preferable to allow the gel to form preferably for at least 5-10 minutes or more preferably for at least 10-30 minutes before opening the device to expose the hydrated gel. Optionally, the method further comprises placing a coated surface of the reagent strip 580 in contact with the hydrated gel. In this process, the cover sheet 330 is lifted to expose the hydrated gel, the reagent strip 580 is positioned in and/or near the aperture 357 in the sample housing 360, and the cover sheet 330 is lowered to bring the reagent strip into contact with the hydrated gel. The sample housing 360 is then incubated for a period of time, after which the device is observed for an indicator of microbial growth. The device is typically incubated at temperatures from 20-45° C., preferably 25-37° C. The device is incubated for a period of time (e.g., 18-48 hours, depending on the growth rate of the target microorganisms and the indicator system) to allow the number of microorganisms present in the sample to increase and/or to allow the metabolic activity of the microorganisms to cause a detectable change in an indicator. In certain embodiments, the microorganisms form discrete colonies in the hydrated gel. The number of microorganisms in the original sample may be enumerated by counting colonies.

EXAMPLES

Example 1

Detection and Enumeration of Listeria innocua from a Surface

Preparation of Reagent Strips

Liquid growth media for the growth and detection of Listeria species was made according to the formula listed in Table 1. The enzyme inducer (1-O-methyl-α-D-mannopyranoside) and chromogenic enzyme substrate (6-Chloro-3-indoxyl-α-D-mannopyranoside) were obtained from Biosynth International (Naperville, Ill.). M150 Ethanol-washed Guar was obtained from Danisco (Kreuzlingen, Switzerland).

TABLE 1

| Broth medium for growth and detection of Listeria species. | |
|---|---|
| Ingredient | Concentration (g/L) |
| Pancreatic Digest of Casein | 10.0 |
| Proteose Peptone #3 | 10.0 |
| Nalidixic Acid | 0.036 |
| Acriflavin | 0.03 |
| Moxalactam | 0.03 |
| Polymyxin B Sulfate (7690 units/mg) | 0.001 |
| Yeast Extract | 8.0 |
| Sodium Chloride | 40.0 |
| Lithium Chloride | 4.5 |
| Disodium Phosphate | 12.0 |
| Monopotassium phosphate | 6.0 |
| 1-O-methyl-α-D-mannopyranoside | 5.0 |
| 6-Chloro-3-indoxyl-α-D-mannopyranoside | 2.0 |
| Xanthan gum | 8.0 |
| M150 Ethanol-washed Guar | 4.0 |

The substrate used for coating the reagent strip was 8.5" wide, 2.91 mil (0.07 mm) thick clear polyester film. The liquid media was coated on the first side of the substrate using a knife coater with a 7 mil (0.18 mm) gap and subsequently passing the coated substrate through a drying oven set at approximately 230° F. (110° C.). The oven drying time was approximately two and half minutes. The coating and drying procedure was repeated on the opposite side of the substrate, resulting in a plastic film that was coated on both sides with the same growth medium. The approximate coating weight for each side of the coated film was 0.230 g/24 in$^2$ (0.230 g/155 cm$^2$). The double-coated substrate was die cut into circles, each circle having a diameter of 2.875 in. (7.30 cm).

Preparation of the Sample Housing Devices

Sample housing devices were constructed by assembling the following components into a single unit: a bottom member, a foam spacer, a barrier layer, and a cover sheet. The foam spacer was attached to the bottom member by an adhesive that was coated onto the bottom member, as described below. The barrier layer was attached along one edge of the foam spacer using ⅜ in. (9.5 mm)-wide double-sided adhesive tape. The cover film was attached (along the same edge) to the barrier layer using the double-sided adhesive tape. Drawings of this construction can be seen in FIGS. 3A and 3B.

The bottom member consisted of 6.3 mil (0.16 mm) thick polycoated paper (83 pound HD RHI-Lease FA 34 Yellow Grid, Grade 406-83010, obtained from Wausau-Mosinee Paper Corp., Rhinelander, Wis.). A yellow grid (perpendicular lines spaced 1 cm apart over the entire area) was printed onto the non-silicone-treated ("bottom") side of the paper. The silicone-treated ("top") side of the paper was coated with an iso-octyl acrylate/acrylamide copolymer adhesive (96 wt. % iso-octyl acrylate and 4 wt. % acrylamide obtained from 3M Company, St. Paul, Minn.; coating weight approximately 145-200 mg/200 cm$^2$).

The spacer consisted of polystyrene foam material (CL3V Capliner, White, 8.5 inches (21.6 cm) wide, 20 mil (0.51 mm) thick; obtained from American Fuji Seal, Bardstown, Ky.). A 2.875 inch (7.30 cm) circle was die cut and removed from the spacer material. The spacer material was then laminated to the adhesive coated side of the bottom member by running the bottom member and die-cut spacer through a nip roller. The circle cut out of the spacer material formed a circular depression or "well" and the bottom member formed the bottom surface of the well in the laminate, as shown in FIG. 3A.

The barrier film consisted of polyester (200 gauge polyester film, Color K399 Light Blue, obtained from CPFilms Inc., Martinsville, Va.). A release was coated on one side of the barrier film. The barrier film was attached along one edge of the foam spacer using double-sided adhesive tape such that the release coated side of the barrier film was facing the bottom member.

The cover sheet was constructed from a 1.6 mil (0.04 mm) thick biaxially-orientated polypropylene (BOPP) film that was previously coated with an iso-octyl acrylate/acrylamide copolymer adhesive (96 wt. % iso-octyl acrylate and 4 wt. % acrylamide, coating weight approximately 165-260 mg/200 cm$^2$). The adhesive coated side of the BOPP film was subsequently coated with M150 non-ethanol washed guar gum powder (obtained from Danisco; powder coating weight approximately 0.30-0.60 g/24 in$^2$ (0.30-0.60 g/155 cm$^2$). The cover sheet was attached to the barrier layer with double sided adhesive tape, as described above.

Preparation of Sample Collectors

Two types of sample collectors were constructed. Type I sample collectors were constructed using clear 3 mil polyester film. The film was die cut into 2.875 inch (7.3 cm) diameter circles. Type II sample collectors were constructed by laminating nonwoven materials to a plastic substrate. For type II sample collectors, a tackified high pressure sensitive iso-octyl acrylate/acrylic acid copolymer adhesive (96 wt. % iso-octyl acrylate and 4 wt. % acrylic acid, Part Number AZ-1229, 3M Company, St. Paul, Minn., coating thickness was approximately 2 mils (0.05 mm)) was laminated to a 5 mil (0.13 mm) thick white polyester film (226Melinex, obtained from DuPont Teijin Films, Hopewell, Va.) and an absorbent material (shown in Table 2) was subsequently laminated onto the adhesive. After the laminates were made, the type II sample collectors were die cut into 2.875 inch (7.24 cm) diameter circles. Table 2 lists the sample collectors used in these experiments.

TABLE 2

Sample Collectors

| Sample Collector | Description | Type | Nonwoven |
|---|---|---|---|
| A | 3 mil (0.08 mm) clear polyester film | I | None |
| B | Polyester laminate | II | Knitted Loop (Style No. WW1112, Gehring Textiles, Inc., Garden City, NY) |
| C | Polyester laminate | II | 40 HEX VisPore Film (0.000125 inch caliper, Tredegar Film Products, Richmond, VA) |

Preparation of Inoculated Surfaces

*Listeria innocua* (ATCC#33091) was grown in tryptic soy broth with 0.6% yeast extract overnight at 35° C. Seventy-five microliters of the overnight culture was diluted into 50 mL of tryptic soy broth with 0.6% yeast extract. The suspension was shaken and two 0.5 mL samples were spread over 4×4 inch sections of flat, sterile stainless steel using a sterile Dacron polyester tipped applicator. The stainless steel surfaces were allowed to dry at room temperature. After the steel surfaces were dry, the devices described above were used to collect and quantify the microbes on the surface of the stainless steel.

Surface Testing Procedure

The experimental procedure described below was evaluated in comparison to a standard method, which consisted of i) a sponge premoistened with neutralizing buffer (Nasco, 18-oz. Whirl-Pak Hydrated Speci-Sponge Bag, Product ID—BO1422WA, from Hardy Diagnostics, Santa Maria, Calif.) was rubbed over a 4 inch by 4 inch (103 cm$^2$) inoculated area and placed into the bag from which it came, ii) five milliliters of buffered peptone water was added to the bag containing the sponge and the bag was manually massaged for approximately 30 seconds to release the bacteria from the sponge, iii) the bag containing the sponge and buffered peptone water was allowed to stand at room temperature for 1-1.5 hours, iv) three milliliters of the liquid suspension was removed from the bag using a pipette and was dispensed into a Petrifilm™ Environmental *Listeria* plate (3M Company, St. Paul, Minn.), and v) the Petrifilm plate was incubated and the appearance of any bacterial colonies was interpreted according to the manufacturer's instructions.

In the experimental procedure, the sample collector was rubbed over the 4 inch by 4 inch (103 cm$^2$) section of the inoculated, dried stainless steel surface for a period of 30 to 60 seconds. In some instances, the sample collector was dry. In other instances, the sample collector was premoistened by applying a light aerosol (approximately 0.5-1.0 milliliters of buffered peptone water) to the sample collector using a spray bottle).

The sample collector was placed into the sample housing in the "well" formed by the foam spacer, with the sample-side facing upward (toward the polyester barrier layer). The sample housing was subsequently held at room temperature for approximately 25 minutes. The cover film and barrier film were lifted off the foam spacer, the barrier film was removed, and 3 mLs of buffered peptone water was pipetted onto the sample collector. The cover film was reattached to the foam spacer with double sided adhesive tape and the cover film was subsequently lowered onto the foam spacer, bringing the powdered guar gum into contact with the buffered peptone water to form a gel. The sample housing was kept on a level surface for approximately 60 minutes to allow for some growth of the microorganisms. Afterward, the cover film was lifted and the double-coated reagent strip was inserted into the sample housing such that one side of the reagent strip contacted the sample collector and the other side contacted the hydrated portion of the cover film. The sample housing was then placed into an incubator at 35° C. for 26 hours. The reagent strip was examined for the presence of bacterial colonies (which typically appeared as small dots of various sizes, having varying shades of reddish color). The results of this test are shown in Table 3 and Table 4.

TABLE 3

Microbial Counts (Each number represents a colony count from a single plate.)

| Sample Collector Material | Colony Forming Units/Sample | |
|---|---|---|
| | Dry Sample Collector | Wet Sample Collector |
| Standard Method | NA | 29 |
| Polyester Film | 0 | 70 |
| Knitted Loop | 35 | 32 |
| 40 HEX VisPore Film | 17 | 41 |

TABLE 4

Colony Appearance

| Sample Collector Material | Colony Appearance after 26 Hrs. of Incubation | |
|---|---|---|
| | Dry Sample Collector | Wet Sample Collector |
| Polyester Film - 3 mil | No visible colonies. | Colonies were the same size, shape, and color (red) as the standard method. |
| Knitted Loop | Colonies were approximately the same size and shape as the standard method, although the colony color was a lighter shade of red and the colony margins were less distinct than the colonies observed in the standard method. | Colonies were the same size, shape, and color as the standard method. |

TABLE 4-continued

Colony Appearance

| Sample Collector Material | Colony Appearance after 26 Hrs. of Incubation | |
|---|---|---|
| | Dry Sample Collector | Wet Sample Collector |
| 40 HEX VisPore Film | Colonies were approximately the same size and shape as the standard method, although the colony color was a lighter shade of red and the colony margins were less distinct than the colonies observed in the standard method. | Colonies were approximately the same size and shape as the standard method, although the colony color was a lighter shade of red and the colony margins were less distinct than the colonies observed in the standard method. |

Example 2

Detection and Enumeration of Staphylococcus aureus from a Surface

Preparation of the Sample Housing Devices

The sample housing devices used in this experiment were 3M PETRIFILM Staph Express (STX) Count System plates obtained from 3M Company (St. Paul, Minn.). The dry media in each plate was hydrated with 1 milliliter of Butterfield's phosphate diluent and was allowed to gel prior to using the plates in this experiment.

Preparation of Sample Collectors

Type I sample collectors were constructed using clear 3 mil polyester film as described in Example 1. Type II sample collectors were constructed by laminating the designated bonded material (e.g., cheesecloth) to clear 3 mil polyethylene film using a pressure-sensitive acrylic-based adhesive. CEREX G192988 nonwoven material was obtained from CEREX Advanced Fabrics (Cantonment, Fla.). Hanes Wetlaid Hydroguard 150 HEM PET/cellulose was obtained from Hanes Industries (Conover, N.C.). The Hanes material was pretreated with SPAN 20 (obtained from Uniquema, Sanford, Stanford, Fla.) to make it hydrophilic. The pretreatment consisted of wiping the fabric material with solution of SPAN-20 (2.5% w/v SPAN-20-sorbitan monolaurate in 97.5% w/v isopropyl alcohol) until the fabric was saturated with the solution. The fabric was allowed to air dry at room temperature. A portion of the treated fabric was tested by transferring a few drops of water onto a surface of the fabric to observe that the water was absorbed (wicked) into the fabric.

Preparation of Inoculated Surfaces

*Staphylococcus aureus* ATCC 25923 was grown in tryptic soy broth for 18 hours at 35° C. Twenty microliters of the overnight culture was diluted into 99 mL of Butterfield's phosphate diluent and the resulting mixture was shaken to uniformly distribute the bacteria in suspension. One milliliter of the buffered bacterial suspension was transferred to a second bottle (99 mL) of Butterfield's phosphate diluent. The diluted suspension was shaken and three 0.5 mL samples were spread over 4×4 inch sections of separate flat, sterile stainless steel coupons using a sterile glass spreader. The stainless steel surfaces were allowed to dry at room temperature for 30-60 minutes in a laminar flow hood. It was estimated that each stainless steel coupon was inoculated with approximately 60 colony-forming units (CFU) of *S. aureus* cells in this procedure. After the steel surfaces are dry, the sample collectors described above were used to collect and quantify the microbes on the surface of the stainless steel.

Surface Testing Procedure

The sample collectors were moistened by applying a light aerosol of Butterfield's phosphate diluent (approximately 0.5-1.0 mL) to the sample collector using a spray bottle. Samples were collected by vigorously rubbing a surface of the sample collector over a 4 inch by 4 inch (103 cm$^2$) section of the inoculated, dried stainless steel surface. The surface was rubbed side-to-side in one direction, and then rubbed side-to-side in a direction that was perpendicular to the direction in which the surface was initially rubbed.

The cover sheet of a prehydrated PETRIFILM STX plate was lifted, exposing the well in the center of the foam spacer (i.e., the gel formed by the dehydrated media remained attached to the cover sheet). The sample collector was placed into the sample housing (in the well formed by the aperture in the foam spacer) with the sample-side facing upward (toward the cover sheet). The cover sheet was lowered, contacting the hydrated gel with the sample on the sample collector. The sample housing was placed into an incubator at 35° C. for about 18 hours and the colonies, which appeared as small red dots, were counted. The number of colonies in each plate is shown in Table 5. The absence of colony forming units in the experiment with a polyethylene film sample as the collector may be due to the loss of viability of the bacteria inoculated onto the test surfaces during the course of the experiment.

TABLE 5

Microbial Counts (Each number represents a colony count from a single plate.)

| Sample Collector Base Material/Bonded Material | Colony Forming Units/Sample |
|---|---|
| Polyethylene Film/None | 0 |
| Polyethylene Film/Cheesecloth | 10 |
| Polyethylene Film/CEREX G192988 | 8 |

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

The invention claimed is:

1. A kit for sampling and enumerating microorganisms, the kit comprising:
   a sample housing comprising
   a bottom member comprising a self-supporting water impervious substrate with upper and lower major surfaces;
   a cover sheet comprising a substrate with upper and lower major surfaces wherein at least part of one major surface of the cover sheet comprises a coating of a cold water soluble powder including at least one gelling agent; and
   a water-impermeable barrier layer attached to the bottom member or the cover sheet, wherein the barrier layer is positioned between the cover sheet and the bottom member;
   wherein the cover sheet is attached to the bottom member and wherein the powder faces the upper major surface of the bottom member.

2. The kit according to claim 1, further comprising a sample collector with upper and lower major surfaces substantially free of hydrophilic agents, wherein at least one major surface of the sample collector is water-impervious, wherein at least one major surface of the sample collector comprises a porous material.

3. The kit according to claim 1, further including a reagent strip comprising a self-supporting substrate with upper and lower major surfaces wherein at least part of one major surface of the reagent strip comprises a coating of a cold water soluble gelling agent and a hydrophilic agent selected from the group consisting of a nutrient for growing microorganisms, a selective agent, an indicator, and combinations of any two or more of the foregoing.

4. The kit according to claim 1, wherein a portion of the barrier layer is detachably attached to the sample housing.

5. The kit according to claim 1, wherein at least one major surface of the sample collector further comprises a porous material.

6. The kit according to claim 1, wherein the sample housing further comprises a spacer containing an aperture wherein the spacer is adhered to the upper surface of the bottom member.

7. The kit according to claim 1, wherein the sample collector further comprises a tab.

8. The kit according to claim 7, wherein the tab is detachable.

* * * * *